United States Patent [19]

Gillilan

[11] Patent Number: 4,737,149
[45] Date of Patent: Apr. 12, 1988

[54] SYRINGE NEEDLE SHIELD

[76] Inventor: Thomas A. Gillilan, 1421 W. 25th St., Long Beach, Calif. 90810

[21] Appl. No.: 45,385

[22] Filed: May 4, 1987

Related U.S. Application Data

[63] Continuation-in-part of Ser. No. 864,533, May 19, 1986.

[51] Int. Cl.$^4$ .............................................. A61M 5/32
[52] U.S. Cl. ..................................... 604/192; 604/263
[58] Field of Search ....................... 604/192, 263, 187

[56] References Cited

U.S. PATENT DOCUMENTS 4,485,918 12/1984 Mayer ............................ 604/263 X
4,596,562 6/1986 Vernon ............................... 604/192

Primary Examiner—John D. Yasko
Attorney, Agent, or Firm—I. Michael Bak-Boychuk

[57] ABSTRACT

A resilient shield assembly for use in engaging a protective sheath releasably mounted on a syringe needle assembly the assembly including a resilient annular shield joined to a resilient tubular handle depending from one side of the annulus. The interior dimensions of the tubular handle are selected for resilient grasping of the sheath. In one implementation the handle may include a central ejection element aligned to oppose the inserted sheath while in another example both ends of the handle are open.

2 Claims, 2 Drawing Sheets

SYRINGE NEEDLE SHIELD

REFERENCE TO RELATED APPLICATIONS

This application is a continuation-in-part of patent application Ser. No. 864.533 and applicant claims the earlier filing date of May 19, 1986 for the matter common therein.

BACKGROUND OF THE INVENTION

1. Field of the Invention

The present invention relates to syringe cap retention devices and more particularly to shielded syringe needle holders for protecting the user.

2. Description of the Prior Art

Today's medical care often entails the use of syringes or other piercing devices for introducing medication into the body of a patient or for withdrawing fluids for analysis. Accordingly, the medical practitioner or those in the practitioner's assisting staff are often exposed to the risk of inadvertent injury, a risk of substantial consequence in the case of treatment of contagious diseases.

As result, techniques were devised in the past which assist in the attachment or removal of either the syringe needle sheaths or the whole needle assembly. One such technique is implemented in a container assembly sold under the model number 8900 by Sage Products, Inc., 680 Industrial Drive, Cary, Ill. 60013.

These techniques, while suitable for their intended purpose, are part of a larger procedure and thus are not always available at the bedside of the patient. A technique and devices which are conveniently carried by the attending personnel are, therefore, desired and it is one such technique that is disclosed herein.

SUMMARY OF THE INVENTION

Accordingly, it is the general purpose and object of the present invention to provide a portable, shielded, syringe needle sheath retainer useful to remove or attach a needle assembly to a syringe.

Other objects of the invention are to provide a shield protecting the attending person from injury in the course of manipulation of a syringe needle assembly.

Yet further objects of the invention are to provide a flexible shielding structure for use in attachment and removal of sheathed syringe needles.

Briefly, these and other objects are accomplished according to one example of the present invention by providing a resilient structure comprising an annular shield extending from the open end of a bore communicating into the interior of an enlarged, bulbous handle. A substantially rigid cylindrical ejection element is adhesively fixed to the other end of the handle presenting an ejection post towards the bore.

The bore itself is dimensionally conformed to engage at one point, by resilient expansion, the exterior of a conventional sheath mounted on the needle assembly of a syringe and thus allows for the removal of the sheath or the rotary manipulation of the sheath and needle assembly in the course of attachment or removal thereof. Once separated from the syringe the sheathed needle cartridge may be ejected from the bore into a collection container by applying force to the ejection element at the opposing surface of the bulb, to press the cylindrical ejection rod against the inserted sheath and, with the aid of the air concurrently compressed within the bulbous handle, to eject the cartridge.

The person attending a patient is thus protected by the annular shield from the sharp needle end through the full sequence of needle mounting, sheath removal and replacement and needle disposal, a sequence heretofore entailing some risks of inadvertent injury and consequent infection.

In an alternative example a resilient tubular segment extends from the center of a dished, annular shield with both ends of the central opening of the segment being conformed to receive, in stretched deformation, the sheathde end of a syringe. This example is particularly suited for use with flat work surfaces adjacent the patient, in the manner of a suction cup, or as a portable shield on insertion into the shield annulus.

In each instance substantial convenience and safety are achieved in an inexpensive article conveniently carried by personnel attending a patient.

Yet a further alternative of the inventive shield is effected by a rectangular pad of two polymeric layers, the first being somewhat rigid and the second of foam rubber construction. These layers included a common tapered opening with the distal surface of the foam layer being slightly dished to form a feathered contact edge at its periphery.

Thus, when laid on a flat surface the foam layer effects frictioned contact somewhat similar to a suction cup. In this alignment the central opening is then presented to the user for receiving the syringe cap. When inverted, however, the taper in the opening terminating at the feathered edge grasps the cap for retention.

BRIEF DESCRIPTION OF THE DRAWINGS

FIG. 3 is yet another sectional view illustrating the collapse deformation of the inventive shield illustrated in FIG. 2;

DESCRIPTION OF THE PREFERRED EMBODIMENTS

Figure 1:
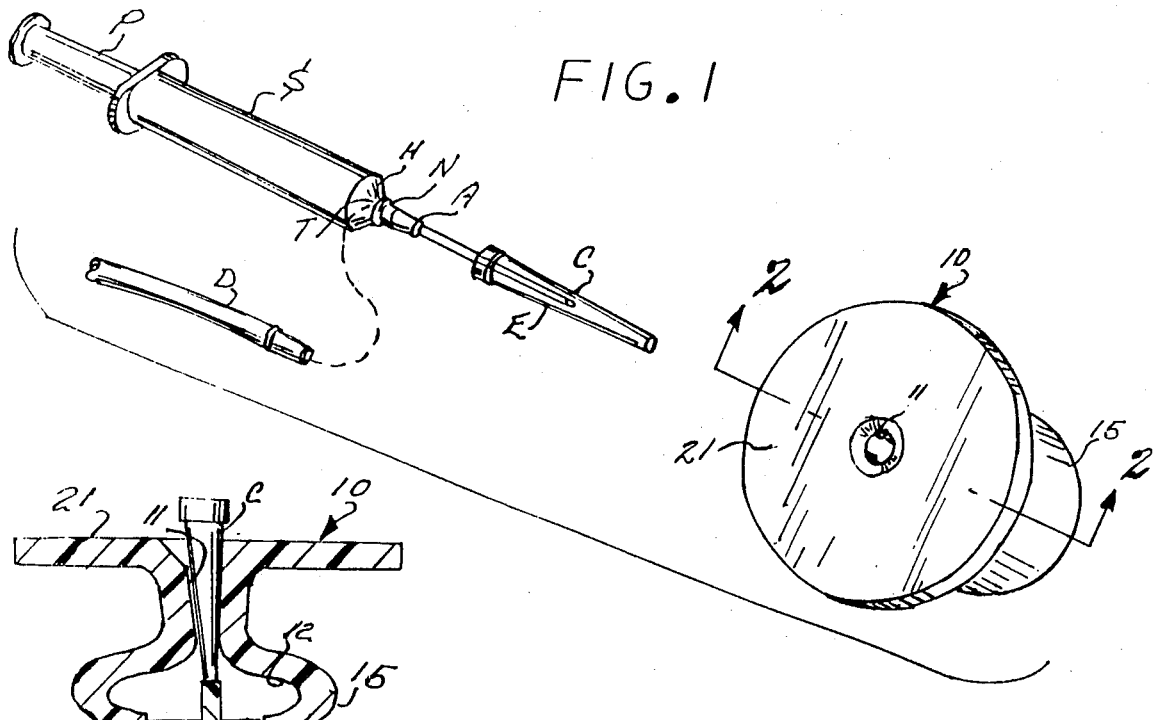
FIG. 1 is a perspective illustration of the inventive shield assembly in the course of use with a conventional syringe.
Figure 2:
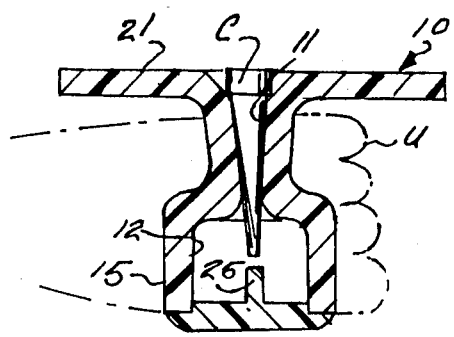
FIG. 2 is a sectional view taken along line 2—2 of FIG. 1.

As shown in FIGS. 1-3 a conventional syringe assembly S typically includes a syringe housing H containing a piston assembly P for expelling or drawing fluid through an end opening N. The exterior surface of housing H, adjacent opening N, includes threaded deformations, or similar attachment provisions, for engaging a needle assembly A.

In conventional practice a sheath or cover C is conformed to surround the needle assembly in releasable engagement therewith, the sheath C including exterior surface elements E for manipulation. These structural features effect manipulative convenience in the course of mounting and removal of the needle assembly onto the end of housing H. Accordingly, selective attachment of the needle is rendered possible which may be mated to other devices like an intravenous feed device D.

In each instance the manipulative sequence of removing and reinstalling the sheath C onto the needle assembly A presents soae risk to the person performing the task. The consequent risks of infection are therefore large and the reduction of these risks is desired.

In accordance with the present invention, a manipulative device generally designated by the numeral 10, is provided with a central bore 11 communicating into the interior cavity 12 of a bulbous handle 15. The exposed opening of bore 11 emerges as the annulus in an enlarged circular shield or disk 21 extending from the periphery of handle 15 such that upon grasping of the handle the hand of the user U is shielded. In this arrangement bore 11 is formed with an inwardly reducing taper from a countersunk opening 22. This taper is selected to be slightly greater than the taper of the exterior surfaces of the sheath C. Thus, by forming the foregoing structure from an elastic, resilient material deformation of the bore surfaces will occur at one point of the exterior of sheath C.

In this manner resilient engagement is assured between the bore surfaces and the surfaces of the sheath, allowing manipulation of the sheath for engagement or disengagement with the needle assembly A or to attach or remove the sheathed needle from the syringe housing H. This retention is conveniently released by a release element 25 fixed across the other end of cavity 12 and provided with a post 26 directed towards the bore 11 by the simple application of external manual pressure against the base thereof. Once the sheath is thus disengaged from this resilient engagement further external pressure to the handle 15 will result in the expulsion of air from the cavity to expel the sheath with the needle assembly into any disposal receptacle.

The foregoing assembly may be made of any one of many resilient polymer structures like vinylon or polyurethane which typically exhibit substantially larger resistance to piercing than that of human physiology. A trained attendant will thus find convenient protection, protection particularly sought when dealing with highly infectious patients.

Figure 4:
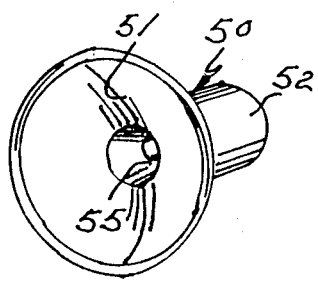
FIG. 4 is yet another perspective illustration of an alternative embodiment of the inventive shield disclosed herein.
Figure 5:
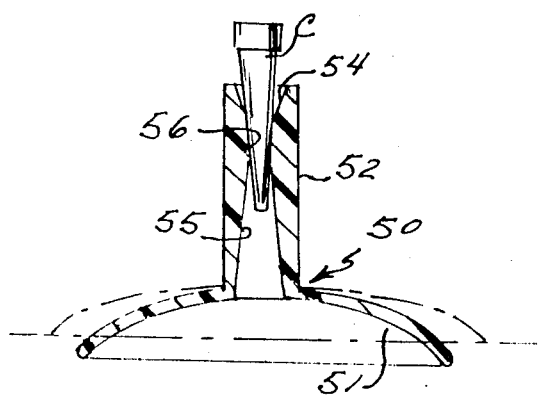
FIG. 5 is a sectional view illustrating the use of the shield shown in FIG. 4 in a first direction.
Figure 6:
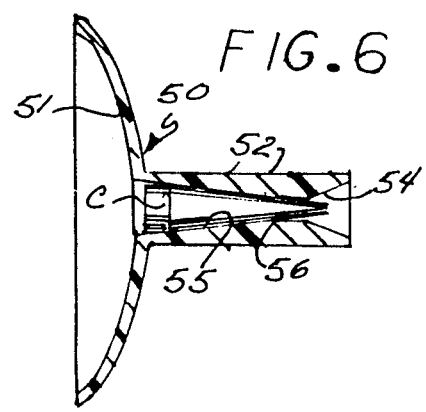
FIG. 6 is a sectional view illustrating the use of the shield shown in FIG. 4 in a second direction.

In an alternative implementation, shown in FIGS. 4, 5 and 6, a device generally designated at 50, comprises a concave, dishlike annular shield 51 including at the center thereof a tubular projection 52. This tubular projection includes an interior bore 53 extending therethrough defined by two opposed tapered segments 54 and 55 joining at a reduced bore section 56. Once again, each taper of segments 54 and 55 is selected to be greater than the exterior taper of the sheath C with a resulting resilient grasping thereof in the course of use.

In this implementation the tapered bore segment 55 communicates into the dished annulus of the shield 51 and segment 54 extends into the free end of the projection 52. By selecting the axial length of segment 54 to be substantially less than the length of segment 55 a configuration is achieved wherein the end of sheath C will extend out of the end of the projection when inserted through the shield annulus and will not extend into the shield if inserted from the other side. The user can select the manipulative functions available either using the device 50 as a shield or as a suction cup against any flat surface F.

Accordingly, an inexpensive, convenient mechanism is provided which may be used in complement with the presently available needle cartridges and which may be discarded without substantial economic consequence.

Figure 7:
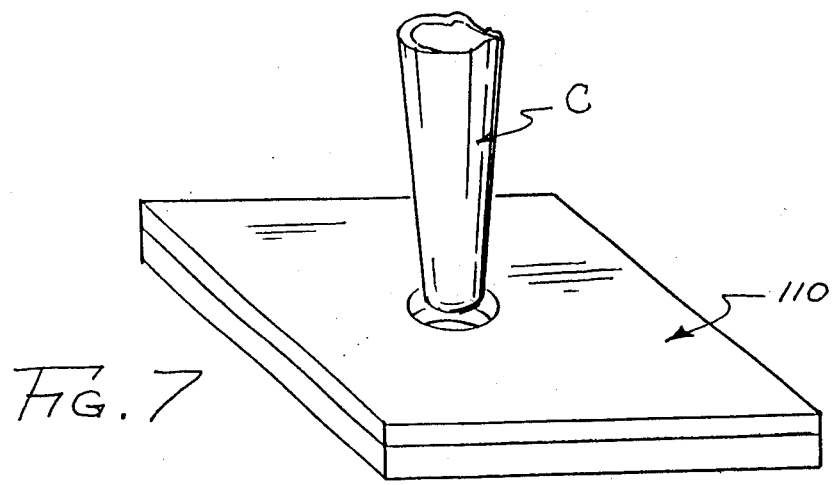
FIG. 7 is a perspective illustration of a further alternative of the inventive syringe shield according to the present invention.
Figure 8:
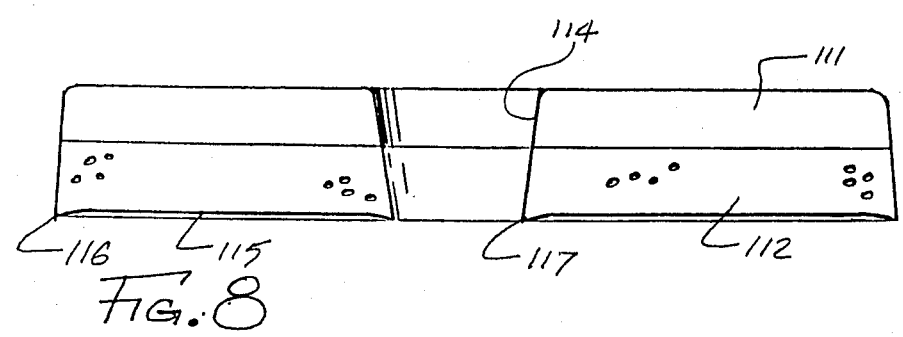
FIG. 8 is a side view, in section, taken along line 8—8 of FIG. 7.
Figure 9:
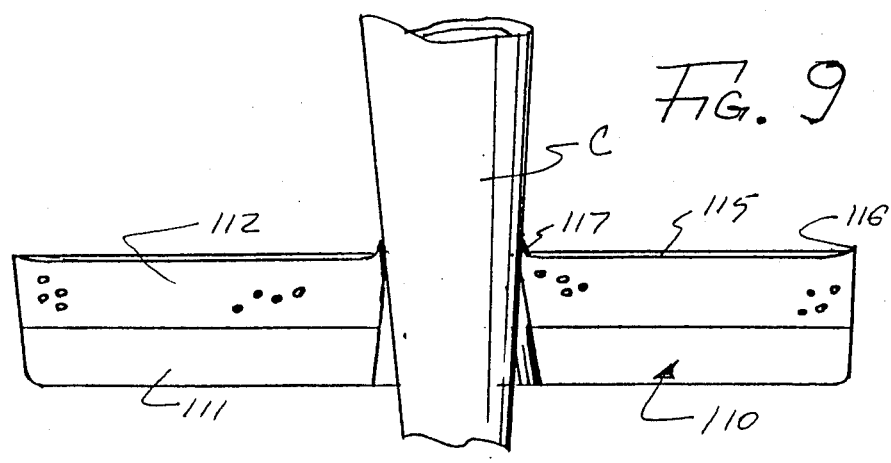
FIG. 9 is a view like that shown in FIG. 8 illustrating the use of the inventive shield in its inverted alignment.

In accordance with a further implementation, shown in FIGS. 7-9, a syringe shield in the form of a rectangular pad is generally shown at 110. As shown, pad 110 comprises an upper polymeric layer 111 contiguously adhered to a lower polymeric layer 112 which is of a foamed construction. The upper layer 111 forms a rigid structure, of some mass, being cast or formed to sufficient thickness for handling. A central opening 114 extends on a decreasing taper through layers 111 and 112 and is conformed to engage the peripheral surfaces of the tip of the cap C. To render such insertion convenient opening 114 is faired at the exterior surface of layer 111.

The exterior surface 115 of the foam layer 112 is conversely dished to define feathered edges 116 and 117 at its peripheries. Edge 117, at the periphery of opening 114, is somewhat smaller than the tip section of the cap C and will thus grasp the cap by expansion when inserted from the opposite direction (as per FIG. 9). Thus the pad provided either a support for the cap or a grasping engagement depending on the direction of its use.

Obviously, many modifications and changes may be made to the foregoing without departing from the spirit of the invention. It is therefore intended that the scope of the invention be determined solely on the claims appended hereto.

What is claimed is:

1. A pad for use with a syringe cap comprising:
   a first substantially rectangular layer;
   a second substantially rectangular layer adhesively attached to said first layer said second layer including a concave exterior surface conformed to a feathered edge at the peripheries thereof; and
   a tapered opening extending through said first and second layer and conformed to engage said syringe cap.

2. Apparatus according to claim 1, wherein:
   said first and second layers comprise polymer material structures, said second layer being formed as a foam.